US011459281B2

(12) United States Patent
Vicari et al.

(10) Patent No.: US 11,459,281 B2
(45) Date of Patent: Oct. 4, 2022

(54) METHOD FOR PRODUCING ACETYLENE AND SYNGAS

(71) Applicant: BASF SE, Ludwigshafen am Rhein (DE)

(72) Inventors: Maximilian Vicari, Ludwigshafen (DE); Christian Weichert, Ludwigshafen (DE); Christopher Alec Anderlohr, Ludwigshafen (DE); Wolfgang Reif, Ludwigshafen (DE)

(73) Assignee: BASF SE, Ludwigshafen am Rhein (DE)

( * ) Notice: Subject to any disclaimer, the term of this patent is extended or adjusted under 35 U.S.C. 154(b) by 93 days.

(21) Appl. No.: 17/048,342

(22) PCT Filed: Apr. 8, 2019

(86) PCT No.: PCT/EP2019/058740
§ 371 (c)(1),
(2) Date: Oct. 16, 2020

(87) PCT Pub. No.: WO2019/201632
PCT Pub. Date: Oct. 24, 2019

(65) Prior Publication Data
US 2021/0155564 A1    May 27, 2021

(30) Foreign Application Priority Data

Apr. 17, 2018 (EP) ...................................... 18167720

(51) Int. Cl.
*C07C 2/78* (2006.01)
*C01B 3/36* (2006.01)
*C07C 11/24* (2006.01)

(52) U.S. Cl.
CPC .................. *C07C 2/78* (2013.01); *C01B 3/36* (2013.01); *C01B 2203/0415* (2013.01); *C01B 2203/0877* (2013.01); *C07C 11/24* (2013.01)

(58) Field of Classification Search
CPC .. C07C 2/78; C07C 11/24; C01B 3/36; C01B 2203/0415; C01B 2203/0877;
(Continued)

(56) References Cited

U.S. PATENT DOCUMENTS 5,824,834 A    10/1998  Bachtler et al.
2013/0334464 A1* 12/2013 Vicari ..................... C07C 4/025
                                                    252/373
2015/0336858 A1    11/2015  Vicari et al.

FOREIGN PATENT DOCUMENTS

EP         2 861 527 B1    6/2016
WO    WO 2013/186291 A1   12/2013
WO    WO 2014/111396 A1    7/2014

OTHER PUBLICATIONS

International Search Report dated Jun. 24, 2019 in PCT/EP2019/058740 filed on Apr. 8, 2019, 2 pages.
(Continued)

*Primary Examiner* — Ali Z Fadhel
(74) *Attorney, Agent, or Firm* — Grüneberg and Myers PLLC

(57) ABSTRACT

A process for producing acetylene and syngas by partial oxidation of hydrocarbons with oxygen, involving: separately preheating a hydrocarbon and a oxygen-comprising input stream; mixing in a mass flow ratio of the oxygen-comprising to hydrocarbon stream at an oxygen number no more than 0.31; feeding the streams via a burner block to a combustion chamber and therein partially oxidizing the hydrocarbon(s) to a cracking gas; quenching the cracking gas to 80 to 90° C. downstream by injecting an aqueous quench medium to obtain a process water stream-1 and a
(Continued)

Figure 1:
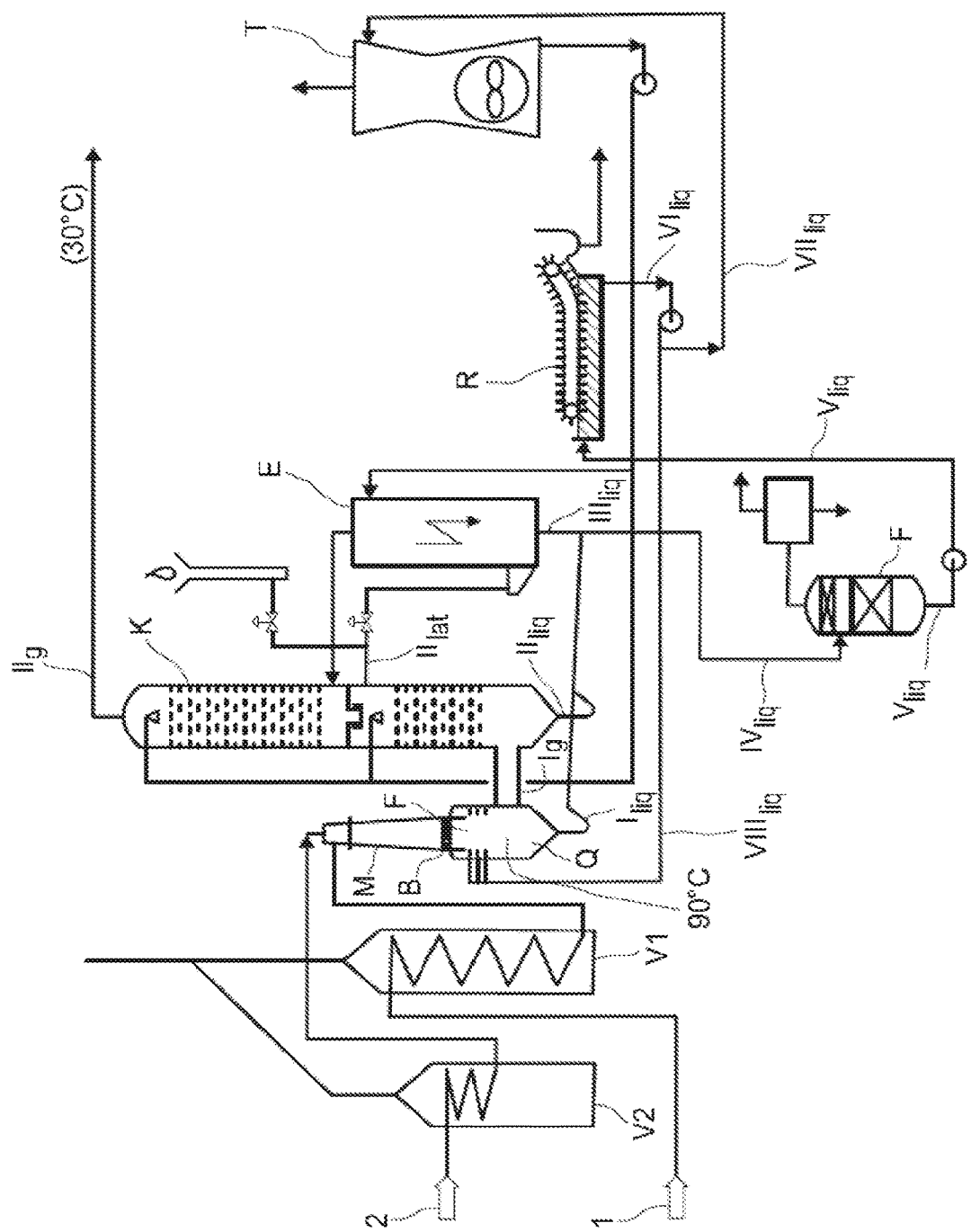

product gas stream-2; cooling the product gas stream-2 in a cooling column by direct heat exchange with cooling water to obtain a process water stream-2 as bottoms, a product gas stream-2 as uppers, and a sidestream; and depleting the sidestream of soot in an electrofilter to generate therein a process water stream-3 combined with water streams-1/2 to afford the process water stream-4.

12 Claims, 2 Drawing Sheets

(58) Field of Classification Search
CPC ........ C01B 2203/048; C01B 2203/049; C01B 2203/0894
See application file for complete search history.

(56) References Cited

OTHER PUBLICATIONS

International Search Report dated Jun. 24, 2019 in PCT/EP2019/058740, 3 pages (English translation previously filed).
International Preliminary Report on Patentability and Written Opinion of the International Searching Authority dated Oct. 20, 2020 in PCT/EP2019/058740 (with English translation) 10 pages.
Peter Passler, et al., "Acetylene" Ullmann's Encyclopedia of Industrial Chemistry, ed. Gerhartz, et al., 5th Edition, vol. A1: Abrasives to Aluminum Oxide, 1985, pp. 97-145.

* cited by examiner

METHOD FOR PRODUCING ACETYLENE AND SYNGAS

The present invention relates to a process for producing acetylene and synthesis gas by partial oxidation of hydrocarbons with oxygen.

The abovementioned partial oxidation is a high-temperature reaction typically performed in a reactor system comprising a mixing means, a burner block and a quenching means and is described for example in Ullmann's Encyclopedia of Industrial Chemistry (5th edition, volume A1, pages 97-144) or U.S. Pat. No. 5,824,834A.

According to Ullmann's Encyclopedia of Industrial Chemistry (5th edition, volume A1, pages 97-144) the heating of the input materials is carried out separately in preheaters. The heated input materials are mixed in a mixing means and, via a mixing diffuser, sent to a burner and on to a combustion chamber. Downstream of the combustion chamber, nozzles are used to supply an aqueous quench medium to the cracking gas, thus cooling it to about 80-90° C. Through suitable choice of the oxygen number $\lambda$ ($\lambda$<0.31), the process is operated such that the yield of acetylene based on the dry cracking gas is optimally high (>8%), wherein the oxygen number $\lambda$ is understood to mean the ratio of the oxygen amount actually present in the second input stream to the stoichiometrically necessary oxygen amount. As is customary, the oxygen number $\lambda$ is the ratio of the actually present oxygen amount to the stoichiometrically necessary oxygen amount required for complete combustion of the input materials. However, this also maximizes the soot loading of the cracking gas. The soot formed from the gas phase in the combustion chamber is partially separated by the quench in a subsequent cooling column and in an electrofilter arranged downstream thereof. The product gas stream containing the value products is separately discharged via the cooling column. Downstream of the electrofilter, the soot concentration in the residual cracking gas (without value products) has fallen to about 1 $mg/m^3$. The soot present in the process water from the quench, the cooling column and the electrofilter has a high hydrocarbon proportion and is therefore hydrophobic, thus making it float on the process water. This soot-laden process water is therefore passed through so-called open soot channels comprising surface particle separators. The floating soot proportions are separated and sent to a furnace. The thus-purified process water is subsequently run through an open cooling tower to be cooled. During this cooling and the preceding solid-liquid separation, a large part of the hydrocarbons bound in the process water in liquid and gaseous form, especially aromatics, alkynes, benzene-toluene-xylene, etc., is emitted into the environment together with portions of the process water. The resulting loss of process water is then compensated by addition and the water circuit is closed towards the cooling column and the quench.

However, emissions of hydrocarbons from the process water from the cooling tower (i.e. in an open process water operating mode) are no longer acceptable under the applicable environmental protection regulations. However, in a closed process water operating mode, the hydrocarbons would accumulate and lead to polymerization and blockage of the system, and so a closed process water mode of operation is not a viable solution either. The open soot channels are a further source of emissions.

A further process for producing acetylene and synthesis gas by partial oxidation of hydrocarbons with oxygen is described in U.S. Pat. No. 5,824,834A. This is a soot-optimized, closed water quench process operated with a lean feed stream, namely with a feed stream having an oxygen number $\lambda$>0.31. However, the process has the disadvantage of a reduced yield of the value product acetylene.

In this process variant, the aqueous quench medium is likewise supplied to the cracking gas using nozzles, thus rapidly cooling said gas to about 80-90° C. The soot formed from the gas phase in the combustion chamber is partially separated by the quench, a subsequent cooling column operated with recirculating water and an electrofilter arranged downstream thereof. The valuable product gas stream is discharged separately via the cooling column. Through choice of the oxygen number $\lambda$ ($\lambda$>0.31), the process is operated such that the amount of soot generated in the cracking gas is sufficiently low that steady-state operation can be ensured solely by discharging the generated reaction water from the combustion. However, this reduces the acetylene content in the dry cracking gas by 2 percentage points compared to the above-described process to about 6% by volume. This makes it possible to achieve a closed water quench procedure separated from the environment. The advantage compared to the above-described process variant is thus the possibility of closed operation without further separation apparatuses. The disadvantage is a loss of yield with regard to the target value product acetylene.

Figure 2:
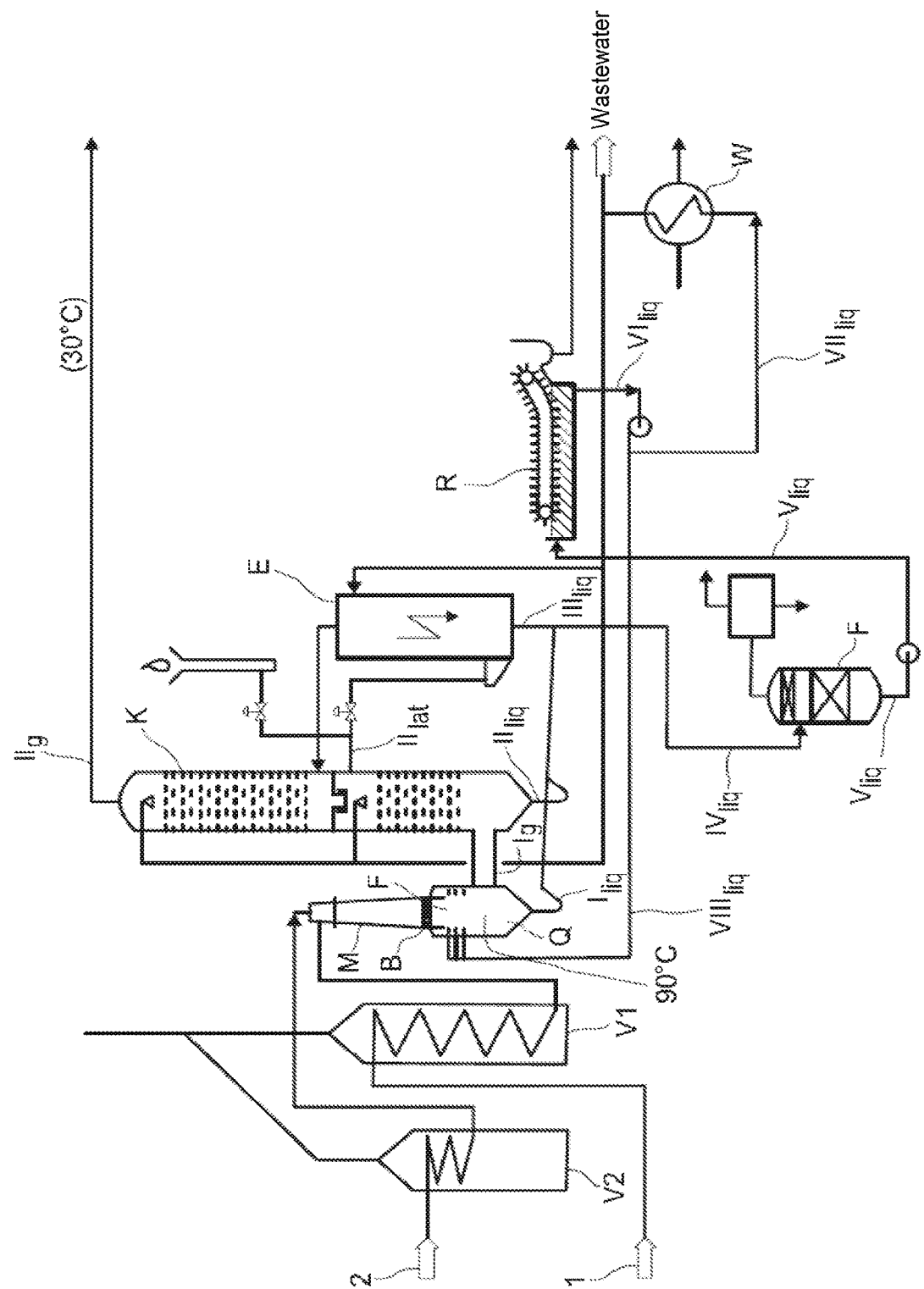

EP 2 861 527 B1 discloses a process for producing acetylene and synthesis gas by partial oxidation of hydrocarbons which combines the advantages of the abovementioned processes and thus allows a high yield of value product acetylene while also markedly reducing the undesired emission of pollutants. In this process, the undesired gases dissolved in the process water stream, which can lead to environmental pollution if allowed to escape in uncontrolled fashion, are advantageously discharged via the gas phase in the decompression vessel (page 3, lines 26 to 33), thus endowing the described process with excellent environmental compatibility. The process water flow is first passed over the soot channels (FIG. 1 and FIG. 2). Since at this point the process water flow still contains the above-described undesired gases in dissolved form, it is necessary to seal the soot channels at great cost and inconvenience, thus impairing the effectiveness of the process.

The present invention accordingly has for its object to provide a process for producing acetylene and synthesis gas by partial oxidation of hydrocarbons which further ensures the advantages of the process described in EP 2 861 527 B1 and moreover ensures the undesired emission of pollutants with high efficiency in a manner that is effective and simple in terms of process engineering.

The object is achieved by a process for producing acetylene and synthesis gas by partial oxidation of hydrocarbons with oxygen, wherein a first input stream comprising one or more hydrocarbons and a second oxygen-comprising input stream are separately preheated, mixed in a ratio of the mass flows of the second input stream to the first input stream corresponding to an oxygen number $\lambda$ of not more than 0.31 as required for complete combustion of the one or more hydrocarbons present in the first input stream, fed via a burner block to a combustion chamber in which the partial oxidation of the hydrocarbons is carried out to obtain a cracking gas which is quenched to 80° C. to 90° C. downstream of the combustion chamber by injection of an aqueous quench medium to obtain a process water stream $I_{liq}$ and
a product gas stream $I_g$ which
is cooled in a cooling column by direct heat exchange with cooling water to obtain
a process water stream $II_{liq}$ as the bottom stream,
a product gas stream $II_g$ as the top stream and
a sidestream $II_{lat}$ which
is depleted of soot in an electrofilter to generate in the electrofilter a process water stream $III_{liq}$ which is combined with the process water streams $I_{liq}$ and $II_{liq}$ to afford the process water stream $IV_{liq}$, wherein the combined process water stream $IV_{liq}$ is subjected to a purification by partial evaporation in a decompression vessel, wherein the combined process water stream $IV_{liq}$ is evaporated in a proportion of 0.01% by weight to 10% by weight based on the total weight thereof to obtain a purified process water stream $V_{liq}$ which is withdrawn at the bottom of the decompression vessel and passed through soot channels having surface particle separators to obtain a process water stream $VI_{liq}$ freed of floating soot which is recycled into the process.

It has been found that a partial evaporation of the combined process water streams in a decompression vessel causes the undesired dissolved gases, especially polymerizable components, for example higher acetylenes, from the process water streams to be entrained into the gas phase with the decompression vapor, thus allowing them to be separated from the liquid phase, the combined process water stream, to such an extent that said stream, of which the excess wastewater generated may also be disposed of, may be recycled into the process.

The integration of the decompression vessel upstream of the soot channels advantageously ensures that the undesired dissolved gases are effectively withdrawn from the process water stream at an early stage. This makes it possible to advantageously avoid costly and inconvenient sealing measures resulting from potential emissions of such undesired dissolved gases in the downstream soot channels and to make the process altogether more effective and economic.

The vapors of undesired dissolved gases entrained in the decompression vapor may subsequently be incinerated or otherwise disposed of in the process after condensation of the water vapor, for example.

It has surprisingly been found that a single-stage decompression for partial evaporation of the combined process water stream in a proportion of 0.01% to 10% by weight, based on the total weight of the combined process water stream, allows sufficient depletion of undesired dissolved components and the process may therefore be operated in a closed process water circuit.

In a preferred embodiment, the process is operated with a closed process water circuit. In this process variant, it is preferable when a substream of the purified process water stream is discharged from the process and the remaining substream of the purified process water stream is recycled into the process. It is preferable when the process water stream $VI_{liq}$ exiting the soot channels is divided up and a substream of this process water stream $VI_{liq}$ is supplied to a heat exchanger as process water stream $VII_{liq}$ and, after cooling, a substream of this cooled process water stream is recycled into the cooling column and the remaining substream is discharged into the wastewater and the second substream of the process water stream $VI_{liq}$ exiting the soot channels is recycled into the quench region below the burner block as process water stream $VIII_{liq}$.

In a further preferred process variant, the process water stream $VI_{liq}$ exiting the soot channels is divided up and a substream of this process water stream $VI_{liq}$ is supplied as process water stream $VII_{liq}$ to a cooling tower and cooled therein and subsequently recycled into the cooling column and the second substream of the process water stream $VI_{liq}$ is recycled as process water stream $VIII_{liq}$ into the quench region below the burner block. In this process variant, it is preferable when the entire purified process water stream is recycled into the process.

The combined process water stream is preferably evaporated in a proportion of 0.5% by weight to 5% by weight based on the total weight thereof.

The process for producing acetylene and synthesis gas is preferably operated with an oxygen number $\lambda$ of not more than 0.31, wherein oxygen number $\lambda$ is understood as meaning the ratio of the oxygen amount actually present in the second input stream to the stoichiometrically necessary oxygen amount required for complete combustion of the one or more hydrocarbons present in the first input stream.

Operation with an oxygen number $\lambda$ in the abovementioned range ensures a high yield of value product acetylene.

The process is independent of the specific configuration of the reactor system comprising the mixing means, the burner block and the quenching means.

The reactor systems typically employed are more particularly elucidated hereinbelow:

The starting materials, i.e. a gas stream comprising hydrocarbon, in particular natural gas, and oxygen are heated separately, typically up to 600° C. The reactants are intensively mixed in a mixing means and, after flowing through a burner block, brought to exothermic reaction. The burner block typically consists of a multiplicity of parallel channels in which the flow rate of the ignitable oxygen/hydrocarbon mixture is higher than the flame rate to prevent penetration of the flame into the mixing means. The metallic burner block is cooled in order to withstand the thermal stresses. There is a risk of pre-ignition or post-ignition depending on the residence time in the mixing means on account of the limited thermal stability of the mixtures. To this end, the term ignition delay time or induction time is used as the timespan over which an ignitable mixture undergoes no appreciable intrinsic thermal change. The induction time depends on the type of the employed hydrocarbons, the mixture state and on pressure and temperature. It determines the maximum residence time of the reactants in the mixing means. Reactants such as hydrogen, liquefied natural gas or light benzine, the use of which is particularly desirable in the synthesis process on account of yield and/or capacity enhancements, feature a comparatively high reactivity and thus low induction time.

The acetylene burners used on a production scale today feature a cylindrical geometry of the combustion chamber. The burner block preferably has hexagonally arranged passage bores. In one embodiment, for example 127 bores of 27 mm internal diameter are arranged hexagonally on a circular base cross section having a diameter of about 500 mm. The employed channel diameters are about 19 to 27 mm in diameter. The subsequent combustion chamber, in which the flame of the acetylene-forming partial oxidation reaction is stabilized, is typically also of cylindrical cross section, is water-cooled and corresponds in appearance to a short pipe (e.g. 180 to 533 mm in diameter and 380 to 450 mm in length). At the height of the burner block, so-called auxiliary oxygen is supplied to the combustion chamber both in the axial direction and in the radial direction. This ensures flame stabilization and thus a defined spacing of the flame base and thus of reaction commencement from reaction termination by the quench unit. The entire burner composed of burner block and combustion chamber is suspended from above via a flange in a quench container of larger cross section. Installed at the height of the exit plane from the combustion chamber on the outer circumference thereof on one or more quench distributor rings are quench nozzles which with or without the aid of an atomization medium atomize the quench medium and inject it virtually perpendicularly to the main flow direction of the reaction gases exiting the combustion chamber. This direct quench has the task of cooling the reaction mixture extremely rapidly so that subsequent reactions, i.e. especially the degradation of acetylene formed, are frozen. The range and distribution of the quench jets are ideally such that the most homogeneous possible temperature distribution is achieved within the shortest possible time.

In addition to acetylene, the present industrial process forms essentially hydrogen, carbon monoxide and soot. The soot particles formed in the flame front may adhere to the combustion chamber side walls as seeds, upon which growth, deposition and encrustation of coke layers occurs under suitable physicochemical conditions.

These deposits are periodically mechanically cleaned off in the region of the combustion chamber walls using a raking means.

The present invention utilizes the fact that, in the abovementioned water quench process, a process water stream $I_{liq}$ (a quench water) is generated at a temperature in the range between 60° C. and 90° C., preferably at a temperature in the range of about 70° C. to 90° C. The thermal energy present allows sufficient separation of undesired dissolved gases by partial evaporation into vacuum.

The partial evaporation is preferably carried out by single-stage decompression into vacuum.

It is more preferable when the partial evaporation is carried out by adiabatic single-stage decompression.

In one process variant, the partial evaporation may advantageously be assisted by heating.

Sufficient separation of the dissolved gases may also be achieved by a stripping column. To this end, the combined process water stream is applied to the top of the column and the stripping vapor added to the bottom of the stripping column in countercurrent. This process step also achieves sufficient depletion of the dissolved gases. The apparatus complexity and thus also the capital costs of the process-engineering step are markedly higher than for simple flashing according to the invention. In addition, the internals of the separation stages and distributors then required have a markedly greater propensity for fouling by polymerizing components than the simple construction of a single-stage decompression.

The decompression vessel is preferably a single-stage unit and may be fitted with customary internals, such as packings or trays, or else with a demister against droplet entrainment.

Also possible is a multistage decompression or a heating of the bottoms such as in a distillation column, instead of preheating of the feed.

This process accordingly provides a very cost-effective option for circuit water purification/wastewater purification.

The vacuum may be generated in a manner known in the prior art, for example via a steam jet apparatus or a water ring compressor. The offgas may then be sent for further treatment within the plant or else sent to an offgas incineration.

The invention is more particularly elucidated hereinbelow with reference to a drawing and in working examples.

In the drawing:

FIG. 1 shows a schematic representation of a preferred inventive plant comprising a cooling tower and FIG. 2 shows a schematic representation of a further preferred plant for performing the inventive process without a cooling tower.

The plant shown in FIG. 1 is supplied with a hydrocarbon-comprising gas stream (1) and an oxygen-comprising gas stream (2), these are preheated separately via preheaters V1 and V2, mixed in a mixing means (M), supplied via a burner block (B) to a combustion chamber (F) and subsequently quenched by injection of an aqueous quench medium in a quench region (Q) to obtain a process water stream $I_{liq}$ and a product gas stream $I_g$.

The product gas stream $I_g$ is cooled by direct heat exchange with cooling water in a cooling column (K) to obtain a process water stream $II_{liq}$ as the bottom stream, a product gas stream $II_g$ as the top stream and a sidestream $II_{lat}$. The sidestream $II_{lat}$ is supplied to an electrofilter (E) and therein depleted of soot to form a process water stream $III_{liq}$. At the top of the electrofilter, the purified gas is discharged and supplied to the cooling column. If required (startup of the plant, disruptions), a stream of the sidestream $II_{lat}$ exiting the cooling column may be sent to a cracking gas flare. The process water streams $I_{liq}$, $II_{liq}$ and $III_{liq}$ are combined to afford process water stream $IV_{liq}$ sent to a single-stage decompression vessel (F) and partially evaporated therein to obtain a purified process water stream $V_{liq}$. This purified process water stream $V_{liq}$ is passed through the soot channels (R) comprising surface particle separators to separate the floating soot. At the top of the decompression vessel, the generated flash vapor and inert constituents are withdrawn and sent to a vacuum plant. The process water stream $VI_{liq}$ exiting the soot channels is divided up and a substream of this process water stream $VI_{liq}$ is supplied as process water stream $VII_{liq}$ to a cooling tower (T) and cooled therein and subsequently recycled into the cooling column (K). A substream of this recycled process water stream is supplied to the upper region of the electrofilter as a washing stream to clean the wires. The second substream of the process water stream $VI_{liq}$ is recycled as process water stream $VIII_{liq}$ into the quench region below the burner block.

The further preferred embodiment shown in FIG. 2 shows a largely analogous plant but with the exception that a heat exchanger (W) is provided in place of the cooling tower (T). The process water stream $VI_{liq}$ exiting the soot channels is divided up and a substream of this process water stream $VI_{liq}$ is supplied to a heat exchanger (W) as process water stream $VII_{liq}$ and, after cooling, a substream of this cooled process water stream is recycled into the cooling column (K) and the remaining substream is discharged into the wastewater and the second substream of the process water stream $VI_{liq}$ exiting the soot channels is recycled into the quench region below the burner block as process water stream $VIII_{liq}$.

WORKING EXAMPLES

Comparative Example

Without process water purification, the open soot channels and the exhaust air from the cooling tower in a plant corresponding to the schematic diagram in FIG. 1 give rise to the following emissions specifically for 1 t of acetylene:

| Open water quench emissions | | | |
|---|---|---|---|
| | Soot channels kg/t Ac | Cooling tower kg/t Ac | Total kg/t Ac |
| CO | 0.303 | 0.486 | 0.789 |
| CH4 | 5.69E−02 | 1.05E−01 | 0.162 |
| C2H6 | 7.66E−03 | 1.47E−02 | 0.022 |
| C2H4 | 7.00E−03 | 2.85E−02 | 0.036 |
| C2H2 | 1.66E−01 | 5.31E+00 | 5.475 |
| PROPENE | 5.30E−04 | 1.91E−03 | 0.002 |
| PROPADIENE | 1.01E−03 | 3.65E−03 | 0.005 |
| PROPYNE | 2.40E−03 | 8.59E−02 | 0.088 |
| BUTENYNE | 1.73E−03 | 3.93E−02 | 0.041 |
| BUTADIENE | 7.58E−03 | 7.05E−01 | 0.712 |
| BENZENE | 2.40E−03 | 1.36E−01 | 0.138 |
| NAPHTHALENE | 5.69E−04 | 1.09E−02 | 0.011 |

INVENTIVE EXAMPLES

The process water purification efficiency is a function of the flash vapor amount as shown in the following table:

To this end, the process water is decompressed from 87.3° C. and 1.013 bar absolute to pressures between 200 mbar absolute and 800 mbar absolute. This partially evaporates the process water in a proportion of 0.0038% to 4.94% by weight. % teilverdampft. This results in the following depletions of dissolved gases as a function of the decompression pressure.

| Depletion by flashing according to pressure (open water quench) | | | | |
|---|---|---|---|---|
| Exit temperature [° C.] | 87.3 | 85.7 | 75.8 | 60.1 |
| Entry temperature [° C.] | 87.4 | 87.4 | 87.2 | 87.1 |
| Entry pressure [bar(absolute)] | 1.013 | 1.013 | 1.013 | 1.013 |
| Exit pressure [mbar(absolute)] | 800 | 600 | 400 | 200 |
| Flash vapor amount based on feed [%] | 0.0038% | 0.3108% | 2.14% | 4.94% |
| | Depletion | Depletion | Depletion | Depletion |
| CO | 87.7% | 99.9% | 99.99% | 100.00% |
| Methane | 84.8% | 99.8% | 99.98% | 100.00% |
| Ethane | 83.9% | 99.8% | 99.98% | 100.00% |
| Ethylene | 63.1% | 99.4% | 99.94% | 99.98% |
| Acetylene | 14.2% | 93.5% | 99.31% | 99.84% |
| Propene | 66.8% | 99.5% | 99.95% | 99.99% |
| Propadiene | 66.8% | 99.5% | 99.95% | 99.99% |
| Propyne | 12.8% | 92.7% | 99.15% | 99.77% |
| Butenyne | 19.1% | 95.4% | 99.47% | 99.86% |
| Butadiene | 5.2% | 82.4% | 97.42% | 99.14% |
| Benzene | 8.4% | 88.9% | 98.66% | 99.62% |
| Naphthalene | 22.1% | 96.1% | 99.56% | 99.88% |

It is clearly apparent that depletion has strong dependence on decompression pressure. Carrying out an inventive, for example single-stage, decompression of the process water upstream of the cooling tower results in only the following emissions to the environment:

The process water enters the single-stage flash stage at 87.4° C. and is decompressed to 400 mbar absolute.

The stream cools from 87.4° C. to 75.8° C. and 2.14% of flash vapor based on the feed are formed. The table additionally shows the depletion in percent effected by the purification step.

| Open water quench with flash emissions | | |
|---|---|---|
| | Cooling tower kg/t | Depletion in % |
| CO | 1.05E−04 | 99.9866% |
| Methane | 2.87E−05 | 99.9823% |
| Ethane | 4.29E−06 | 99.9808% |
| Ethylene | 2.29E−05 | 99.9356% |
| Acetylene | 3.80E−02 | 99.3053% |
| Propene | 1.31E−06 | 99.9462% |
| Propadiene | 2.50E−06 | 99.9463% |
| Propyne | 7.54E−04 | 99.1462% |
| Butenyne | 2.17E−04 | 99.4727% |
| Butadiene | 1.84E−02 | 97.4207% |
| Benzene | 1.84E−03 | 98.6649% |
| Naphthalene | 5.10E−05 | 99.5561% |

Due to the high depletion rate, the cooling tower may be substituted by a closed heat exchanger without the process being subjected to intolerable accumulations of polymerizable components, in particular of higher acetylenes and naphthalene.

| Secondary components in the process water | | |
|---|---|---|
| | Closed water quench Without flash [ppmw] | Closed water quench With flash [ppmw] |
| CO | 2.367 | 0.001 |
| Methane | 0.511 | 0.000 |
| Ethane | 0.071 | 0.000 |
| Ethylene | 0.139 | 0.000 |
| Acetylene | 25.812 | 0.186 |
| Propene | 0.009 | 0.000 |
| Propadiene | 0.018 | 0.000 |
| Propyne | 0.417 | 0.004 |
| Butenyne | 0.191 | 0.001 |
| Butadiene | 3.410 | 0.089 |
| Benzene | 0.018 | 0.009 |
| Naphthalene | 0.053 | 0.000 |

The invention claimed is:

1. A process for producing acetylene and synthesis gas by partial oxidation of one or more hydrocarbons with oxygen, the process comprising:

separately preheating a first input stream comprising a hydrocarbon and a second oxygen-comprising input stream;

mixing the first and second streams in a mass flow ratio of the second to the first input stream at an oxygen number of not more than 0.31, the oxygen number meaning a ratio of an oxygen amount actually present in the second input stream to the stoichiometrically necessary oxygen amount required for complete combustion of hydrocarbons in the first input stream, to obtain a mixed stream;

feeding the mixed stream via a burner block to a combustion chamber in which the hydrocarbons are partially oxidized, thereby obtaining a cracking gas comprising the acetylene and the synthesis gas;

quenching the cracking gas to a temperature in a range of from 80 to 90° C. downstream of the combustion chamber by injection of an aqueous quench medium to obtain a first process water stream $I_{liq}$ and a first product gas stream $I_g$;

cooling the first product gas stream in a cooling column by direct heat exchange with cooling water to obtain a second process water stream $II_{liq}$, as a bottom stream, a second product gas stream $II_g$, as a top stream, and a sidestream;

depleting the sidestream of soot in an electrofilter to generate in the electrofilter a third process water stream $II_{liq}$, which is combined with the first and second process water streams $I_{liq}$ and $II_{liq}$ to afford a fourth process water stream $IV_{liq}$, purifying the fourth process water stream $IV_{liq}$ by partial evaporation in a decompression vessel, wherein the fourth process water stream $IV_{liq}$ is evaporated in a proportion in a range of from 0.01 to 10 wt. % based on total fourth process water stream weight to obtain a purified fifth process water stream $V_{liq}$;

withdrawing the purified fifth process water stream $V_{liq}$ at a bottom of the decompression vessel and passing the purified fifth process water stream $V_{liq}$ through one or more soot channels comprising surface particle separators to obtain a sixth process water stream $VI_{liq}$ freed of floating soot; and recycling the sixth process water stream $VI_{liq}$ into the process.

2. The process of claim 1, wherein the sixth process water stream $VI_{liq}$ is completely recycled into the process.

3. The process of claim 1, further comprising:
dividing up the sixth process water stream $VI_{liq}$ exiting the soot channels into
a first water substream, which is supplied as a seventh process water stream $VII_{liq}$ to a cooling tower and cooled therein and subsequently recycled into the cooling column, and
a second water substream, which is recycled as an eighth process water stream $VIII_{liq}$ into a quench region below the burner block.

4. The process of claim 1, further comprising:
dividing up the sixth process water stream $VI_{liq}$ exiting the soot channels into
a first water substream, which is supplied to a heat exchanger as a seventh process water stream $VII_{liq}$ and, after cooling, obtaining a cooled substream, the cooled substream being recycled into the cooling column and a remaining substream being discharged into a wastewater, and
a second water substream exiting the soot channels, which is recycled into a quench region below the burner block as an eighth process water stream $VIII_{liq}$.

5. The process of claim 1, wherein the fourth process water stream $IV_{liq}$ is evaporated in a proportion in a range of from 0.5 to 5 wt. % based on the total fourth process water stream weight.

6. The process of claim 1, wherein the partial evaporation is carried out by decompression into vacuum.

7. The process of claim 1, wherein the partial evaporation is carried out by decompression into a vacuum in a range of from 50 to 900 mbar a.

8. The process of claim 1, wherein the partial evaporation is carried out by decompression into a vacuum in a range of from 200 to 600 mbar a.

9. The process of claim 1, wherein the partial evaporation is carried out by adiabatic decompression.

10. The process of claim 1, wherein the partial evaporation is assisted by heating.

11. The process of claim 10, wherein the heating is carried out by direct steam injection.

12. The process of claim 1, wherein the first input stream comprises natural gas.

* * * * *